US00PP19832P2

(12) United States Plant Patent
Hart

(10) Patent No.: US PP19,832 P2
(45) Date of Patent: Mar. 17, 2009

(54) ***HELIANTHEMUM* PLANT NAMED 'MAXROSS'**

(50) Latin Name: *Helianthemum nummularium*
Varietal Denomination: Maxross

(76) Inventor: Michael Hart, No. 2 The Cottages, Habberley Road, Worcestershire (GB), DY12 1LA ( * ) Notice: Subject to any disclaimer, the term of this patent is extended or adjusted under 35 U.S.C. 154(b) by 11 days.

(21) Appl. No.: 11/978,294

(22) Filed: Oct. 29, 2007

(51) Int. Cl.
*A01H 5/00* (2006.01)

(52) U.S. Cl. ..... Plt./226
(58) Field of Classification Search ..... Plt./226, Plt./263, 263.1
See application file for complete search history.

*Primary Examiner*—Kent L Bell
(74) *Attorney, Agent, or Firm*—Jondle & Associates, P.C.

(57) ABSTRACT

A new *Helianthemum* plant particularly distinguished as a hardy, evergreen, semi-compact and low-growing shrub with red-purple flowers and yellow stamens, is disclosed.

1 Drawing Sheet

Genus and species: *Helianthemum nummularium.*
Variety denomination: 'Maxross'.

BACKGROUND OF THE NEW PLANT

The present invention comprises a new and distinct cultivar of *Helianthemum,* botanically known as *Helianthemum nummularium* and hereinafter referred to by the cultivar name 'Maxross'. The new cultivar was discovered in Bewdley, Worcestershire, Great Britain in 2000. Both the female and male parents are unknown individual plants of *Helianthemum nummularium.* 'Maxross' was first propagated in the summer and autumn of 2001 in Bewdley, Worcestershire, Great Britain.

The new cultivar was discovered in Bewdley, Worcestershire, Great Britain in 2000 and has been asexually reproduced repeatedly by softwood and semi-hardwood cuttings over a three-year period. The present invention has been found to retain its distinctive characteristics through successive asexual propagations.

SUMMARY OF THE INVENTION

The following are the most outstanding and distinguishing characteristics of this new cultivar when grown under normal horticultural practices in Bewdley, Worcestershire, Great Britain.

1. A hardy, evergreen, semi-compact and low-growing shrub; and
2. Ruby (red-purple) flowers with yellow stamens.

DESCRIPTION OF THE PHOTOGRAPHS

This new *Helianthemum* plant is illustrated by the accompanying photographs which show overall plant habit including blooms, buds, and foliage of the plant; the colors shown are as true as can be reasonably obtained by conventional photographic procedures.

DESCRIPTION OF THE NEW CULTIVAR

Figure 1:
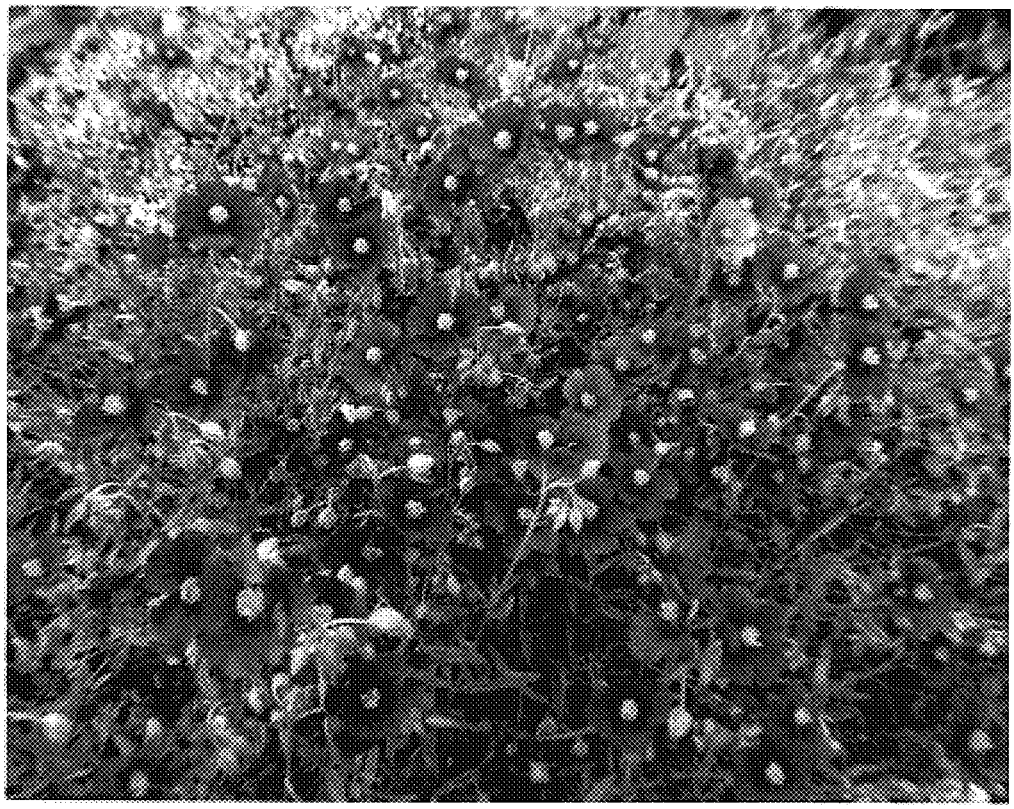
FIG. 1 shows the overall plant habit, including blooms, buds and foliage.
Figure 2:
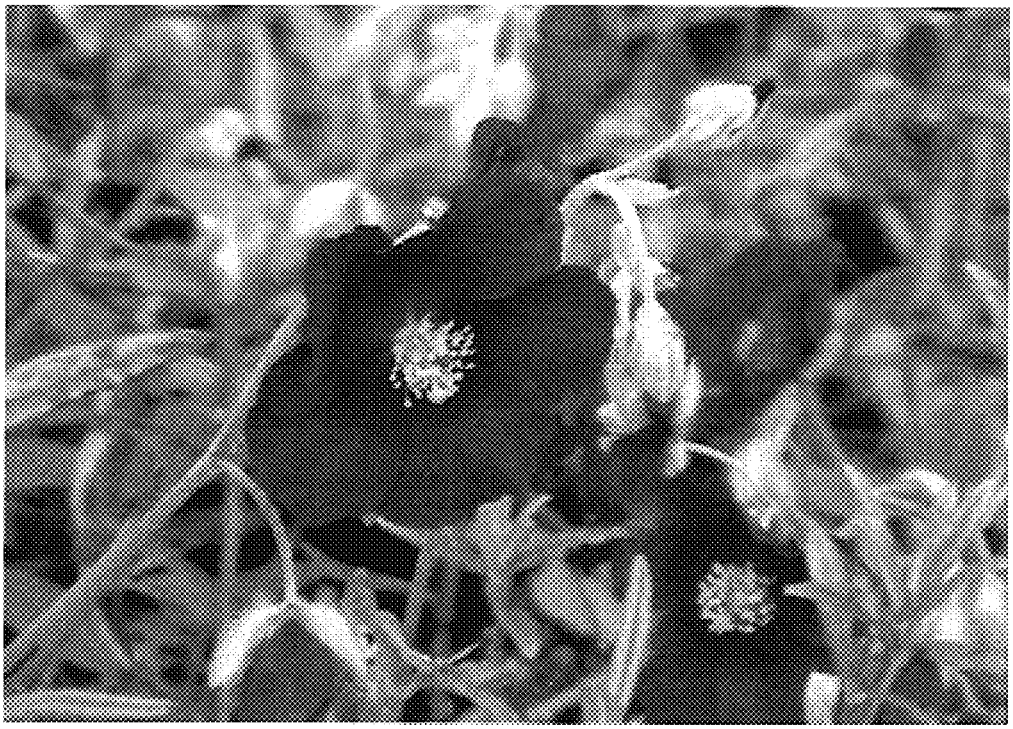
FIG. 2 shows a close-up of a mature flower.

The following detailed descriptions set forth the distinctive characteristics of 'Maxross'. The data which define these characteristics were collected from asexual reproductions carried out in Bewdley, Worcestershire, United Kingdom. The plant history was taken on 2 year old plants grown outdoors. Color readings were taken outdoors under natural light. Color references are primarily to the R.H.S. Colour Chart of The Royal Horticultural Society of London (R.H.S.) (2001 edition).

DESCRIPTION OF THE NEW PLANT

Classification:
- *Family.*—Cistaceae.
- *Botanical.*—*Helianthemum nummularium.*
- *Common name.*—Common rockrose.

Parentage:
- *Female parent.*—An unknown individual plant of *Helianthemum nummularium* (patent status unknown).
- *Male parent.*—An unknown individual plant of *Helianthemum nummularium* (patent status unknown).

Plant:
- *Form.*—Semi-compact.
- *Branching habit.*—Produces many branches per plant.
- *Height.*—20.0 cm to 25.0 cm.
- *Width.*—25.0 cm to 30.0 cm.
- *Time to produce a finished flowering plant.*—9 to 15 months depending on the pot size.
- *Outdoor plant performance.*—'Maxross' is a hardy and excellent dwarf shrub.

Leaves:
- *Arrangement.*—Opposite.
- *Color, immature leaf.*—Upper surface: RHS133A (dark-green). Lower surface: RHS 133B (light-green).
- *Color, mature leaf.*—Upper surface: RHS131B (dark-green) glossy. Lower surface: RHS133B (green).
- *Length.*—2.0 cm.
- *Width.*—0.5 cm.
- *Shape.*—Ensiform, lanceolate.

*Apex.*—Pointed.
*Base.*—Rounded.
*Margin.*—Finely crenate.
*Texture.*—Evergreen.
*Petiole.*—Diameter: 1.0 mm. Color: RHS133C (green). Texture: Smooth.

Stems:
*Color.*—RHS 133D (green) with a light flush of RHS 59B (red-purple) as stems mature.
*Texture.*—Smooth.

Flower buds (just before petals unfold):
*Shape.*—Oval.
*Length.*—1.0 cm.
*Diameter.*—0.5 cm.
*Apex.*—Acute.
*Base.*—Attenuate.
*Color of sepals.*—RHS133C (green) with a light flush of RHS 59C (red).
*Color of petals.*—RHS 59A (red-purple).

Inflorescence:
*Diameter.*—4.0 cm.
*Depth.*—15.0 cm.
*Type.*—Terminal racemes.
*Lastingness of the inflorescence on the plant.*—2 to 4 weeks.
*Peduncle.*—Length: 10.2 cm to 15.2 cm. Diameter: 0.15 cm. Color: RHS 133C (green) with a light flush of RHS 59C (red).

Pedicel:
*Length.*—1.0 cm.
*Diameter.*—1.0 mm.
*Texture.*—Smooth.
*Color.*—RHS 133C (green) with a light flush of 59C (red).

Flower:
*Diameter.*—3.0 cm.
*Depth.*—1.5 cm.
*Form.*—Flat.
*Shape.*—Rounded.
*Color* (*overall*).—RHS 59A (red-purple).
*Number of petals.*—5.
*Lastingness of individual flowers on the plant.*—7 to 10 days depending on the weather.
*Fragrance.*—Absent.

Petals:
*Shape.*—Orbicular.
*Apex.*—Truncate.
*Base.*—Cuneate.
*Margin.*—Entire.
*Length.*—1.0 cm to 1.5 cm.
*Width.*—1.0 cm.
*Color.*—Upper surface: RHS 59A (red-purple). Lower surface: RHS 59C (red-purple).
*Texture.*—Smooth.

Sepals:
*Number.*—3.
*Length.*—0.8 cm to 1.0 cm.
*Width.*—0.5 cm.
*Shape.*—Oval.
*Apex.*—Acute.
*Margin.*—Entire.
*Upper surface.*—RHS 133C (green) with a light flush of RHS 59C (red).
*Lower surface.*—RHS 133C (green) with a light flush of RHS 59C (red).

Reproductive organs:
*Number of anthers.*—Many.
*Filament color.*—RHS 20A (yellow-orange).
*Pollen color.*—RHS 20B (yellow-orange).
*Pollen amount.*—Sparse.
*Stigma color.*—RHS 1B (green-yellow).
*Style color.*—RHS 1B (green-yellow).
*Style length.*—Minute.

Fruit and seed set: Has not been observed.

Disease and insect resistance: Typical of *Helianthemum*.

COMPARISON WITH COMMERCIAL CULTIVARS

'Maxross' differs from the commercial cultivar 'Belgravia Rose' (unpatented) in that 'Maxross' has red-purple flowers, while 'Belgravia Rose' has pink flowers.

'Maxross' differs from the commercial cultivar 'Burgundy Dazzler' (unpatented) in that 'Maxross' has red-purple flowers, while 'Burgundy Dazzler' has burgundy-red flowers.

I claim:

1. A new and distinct cultivar of *Helianthemum* plant as shown and described herein.

* * * * *